United States Patent [19]

Henmi et al.

[11] 4,207,339

[45] Jun. 10, 1980

[54] ANTI-ULCER PHARMACEUTICAL COMPOSITION CONTAINING INOSITOL HEXASULFATE OR AN ALKALINE METAL SALT THEREOF AS ACTIVE INGREDIENT

[75] Inventors: Zen-ichi Henmi, Mobara; Shuichi Arimoto, Joshin; Akira Kotaki, Tokyo; Takafumi Kitano, Mobara, all of Japan

[73] Assignee: Mitsui Toatsu Chemicals Incorporated, Tokyo, Japan

[21] Appl. No.: 940,204

[22] Filed: Sep. 7, 1978

[51] Int. Cl.² ............................................. A61K 31/185
[52] U.S. Cl. ..................................................... 424/315
[58] Field of Search ............................................ 424/315

[56] References Cited

PUBLICATIONS

Chemical Abstracts, vol. 66, (1967), 79569m.
Chemical Abstracts, vol. 67, (1967), 76305g.
Chemical Abstracts, vol. 55, (1961), pp. 3446–3447.

Primary Examiner—Frederick E. Waddell

[57] ABSTRACT

Inositol hexasulfate and its alkaline metal salts have excellent anti-ulcer, antacid and antipeptic effects.

Examination of the action of these compounds on various types of experimental gastric and duodenal ulcers in rats has shown that they have an excellent inhibitory effect on Shay's ulcer, acetic acid ulcer, stress ulcer, cysteamine duodenal ulcer, and aspirin ulcer. In addition, examination of the action of these compounds on the amount of gastric juice secreted, the acidity of gastric juice, and the activity of pepsin in rats has revealed their excellent antacid and antipeptic effects.

2 Claims, No Drawings

ANTI-ULCER PHARMACEUTICAL COMPOSITION CONTAINING INOSITOL HEXASULFATE OR AN ALKALINE METAL SALT THEREOF AS ACTIVE INGREDIENT

BACKGROUND OF THE INVENTION

1. Field of the Invention

This invention relates to anti-ulcer pharmaceutical compositions and, more particularly, to such compositions containing inositol hexasulfate or an alkaline metal salt thereof as an active ingredient.

2. Description of the Prior Art

Inositol hexasulfate is a well-known compound and may usually be prepared by condensing inositol and sulfuric acid with elimination of water. Its alkaline metal salts can be obtained by adding the condensation product dropwise to an aqueous solution of a water-soluble alkaline metal salt (selected from suitable halides, organic carboxylates, nitrates, etc. of alkaline metals).

Although inositol hexasulfate and its alkaline metal salts are expected to have some biological effect or other, their use in medical applications has not been reported as yet.

On the other had, it is well known that the sulfates of sugars have anti-ulcer effects. Nevertheless, there have been no reports concerning the action of inositol and its derivatives on peptic ulcer.

SUMMARY OF THE INVENTION

As a result of intensive research into the pharmacological action of inositol hexasulfate and its alkaline metal salts, the present inventors have found that these compounds have excellent anti-ulcer, antacid and antipeptic effects. Although inositol hexasulfate and its alkaline metal salts are all excellent in anti-ulcer effect, its sodium and potassium salts are particularly preferred because of their stability in the course of preparation.

The term "inositol hexasulfate sodium salt" as used herein denotes the compound having the formula

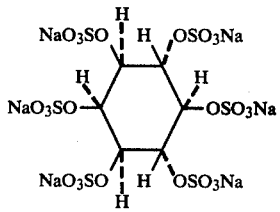

and usually contains 6 molecules of water of crystallization. This salt is a white powder having no definite melting point, easily soluble in water, and very slightly soluble in organic solvents such as absolute ethanol, benzene, etc. On drying at 80° C. for 4 hours under a reduced pressure of 1 mmHg, it loses the water of crystallization to give the anhydrous salt. Its infrared spectrum exhibits absorption peaks at 2.86$\mu$ (OH groups from the water of crystallization), 6.13$\mu$ (C—H bonds) and 8.00$\mu$ (sulfuric ester groups).

The term "inositol hexasulfate potassium salt" as used herein denotes the compound having the formula (I) wherein Na is replaced by K, the compound usually containing 6 molecules of water of crystallization. Its properties are very similar to those of the sodium salt.

An example of the preparation of inositol hexasulfate sodium salt is given below. The potassium salt may also be prepared according to substantially the same procedure.

To 52 ml of 30% fuming sulfuric acid was added 10 g of dry inositol little by little, during which external cooling was used so as to maintain the temperature below 70° C. After completion of the addition, the reaction mixture was heated, stirred at 70° C. for 3 hours, and then allowed to cool. Thereafter, the reaction mixture was added dropwise, with cooling, to a mixture consisting of 25 g of sodium chloride, 100 ml of water and 200 g of ice. The resulting solution was stirred at 0° C. for an hour and, after the addition of 352 ml of methanol, for an additional hour. The precipitated crystals were separated by filtration and dried at 50° C. for 5 hours under a reduced pressure of 40 mmHg to give 55.3 g of a crude product. This crude product was dissolved in 387 ml of distilled water, the resulting solution was filtered to remove any foreign matter, and 387 ml of methanol was then added little by little to the filtrate kept at 60° C. The clear solution thus obtained was cooled to 0° C. and kept at that temperature for 2 hours. The precipitated crystals were separated by filtration and dried at 50° C. for 10 hours under a reduced pressure of 40 mmHg to give 45.1 g of a pure product. Its yield was 90%. Elemental analysis of the product showed that: C, 8.01 (8.00); H, 1.95 (2.01); S, 21.53 (21.36); Na, 15.27 (15.32). The values in parentheses are those calculated for $C_6H_6(OSO_3Na)_6 \cdot 6H_2O$. The infrared spectrum of the product exhibited absorption peaks at 3450, 1630, 1240, 1115, 1065, 1045, 1015, 955, 940, 870, 830, 815, 785 and 680 cm$^{-1}$.

The anti-ulcer, antacid and antipeptic effects of these compounds, together with the acute toxicity thereof, were evaluated by a series of experiments. The inositol hexasulfate sodium and potassium salts used in these experiments both contained 6 molecules of water of crystallization.

(1) Anti-ulcer Effect

The anti-ulcer effect of some compounds of this invention was evaluated with regard to various types of experimental gastric and duodenal ulcers. The results obtained are given in Table 1. The method of evaluation for each type of ulcer is outlined below.

(i) Shay's Ulcer

Male rats of the Wistar strain, 7 or 8 weeks of age, were used in groups of ten. After 48 hours of fasting, the pyloric part of the stomach was ligated under ether anesthesia. Immediately after the operation, a certain amount of a compound to be tested was orally administered to each animal of a group. After 12 hours, the degree of ulceration occurring in the anterior part of the stomach was rated and regarded as an ulcer index (U.I.). Control rats were treated in the same manner as described above, except that they received no compounds to be tested. The results given in Table 1 are expressed in terms of the percentage of inhibition based on the U.I. obtained in the control group.

(ii) Stress Ulcer

Male rats of the Wistar strain, 8 weeks of age, were used in groups of ten. Each animal was immobilized in a stressing cage as developed by Takagi et al., immersed in water at 23° C. to the level of the xiphoid process, and thereby subjected to stress for 16 hours. Thereafter, the stomach was excised. The length of the ulcer formed in the glandular part of the stomach was measured and regarded as an ulcer index (U.I.). A certain amount of a compound to be tested was orally administered just before subjecting the animal to stress. The results are also expressed in terms of the percentage of inhibition based on the U.I. obtained in the control group receiving no compounds to be tested.

(iii) Aspirin Ulcer

Male rats of the Donryu strain, 10 to 11 weeks of age, were used in groups of ten. After 24 hours of fasting, a certain amount of a compound to be tested was orally administered to each animal of a group. Ten minutes later, aspirin was orally administered in a dose of 250 mg/kg. After 6 hours, the size of the ulcer formed in the glandular part of the stomach was rated by visual inspection and regarded as an ulcer index (U.I.). The results are also expressed in terms of the percentage of inhibition based on the U.I. obtained in the control group receiving no compounds to be tested.

(iv) Cysteamine Duodenal Ulcer

Male rats of the Donryu strain, 10 or 11 weeks of age, were used in groups of ten. After 24 hours of fasting, a certain amount of a compound to be tested was orally administered to each animal of a group. Thirty minutes later, cysteamine hydrochloride was orally administered in a dose of 400 mg/kg. After 18 hours, the product of the maximum and minimum diameters of the ulcer formed in the duodenum was determined and regarded as an ulcer index (U.I.). The results are also expressed in terms of the percentage of inhibition based on the U.I. obtained in the control group receiving no compounds to be tested.

(v) Acetic Acid Ulcer

Male rats of the Wistar strain, 6 weeks of age, were used in groups of ten. Under ether anesthesia, each animal was laparotomized, a round frame (with an inside diameter of 5 mm) made of stainless steel was applied to the anterior wall of the stomach, and 100% acetic acid was poured into the frame. After 30 seconds, the acetic acid was removed and the abdomen was closed. Starting on the 7th day after the operation, a certain amount of a compound to be tested was orally administered twice a day to each animal of a group for a period of 7 days. Thereafter, the degree of healing of the ulcer was rated by visual inspection and regarded as an ulcer index (U.I.). The results are also expressed in terms of the percentage of healing based on the U.I. obtained in the control group receiving no compounds to be tested.

Table 1
Inhibitory or Healing Promotion Effect of Some Compounds of This Invention on Various Types of Experimental Ulcers

| Type of Ulcer | Sodium Salt (mg/kg, p.o.) | | | | Potassium Salt (mg/kg, p.o.) | |
|---|---|---|---|---|---|---|
| | 50 | 100 | 250 | 500 | 100 | 250 |
| Shay's Ulcer | 74 | 92 | 77 | — | 85 | 80 |
| Stress Ulcer | — | — | 27 | 50 | — | 25 |
| Aspirin Ulcer | 11 | 44 | 48 | — | 46 | 40 |
| Cysteamine Duodenal Ulcer | — | 37 | 46 | 77 | — | — |
| Acetic Acid Ulcer | — | 29 | 16 | 38 | 28 | 22 |

Notes:
(1)"p.o." stands for "per os (= by mouth)."
(2)The results of the former four experimental ulcers are expressed in terms of the percentage of inhibition, whereas the results of acetic acid ulcer are expressed in terms of the percentage of healing, and in every case greater values indicate better results.

(2) Effect on Gastric Juice Secretion, Gastric Juice Acidity and Pepsin Activity Male rats of the Donryu strain, 11 weeks of age, were used in groups of ten. After 24 hours of fasting, the pyloric part of the stomach was ligated. Four hours later, the gastric juice was collected and its volume was measured. Then, its acidity was determined by titrating an aliquot of the gastric juice with 0.05 N sodium hydroxide. Further, the activity of pepsin was determined by Anson's method. A definite amount (250 mg/kg) of a compound to be tested was orally administered immediately after the pyloric ligation. The results obtained are given in Table 2.

Table 2
Inhibitory Effect of Some Compounds of This Invention on Gastric Juice Secretion, Gastric Juice Acidity and Pepsin Activity

| Test Item | Control Group (solvent alone,p.o) | Sodium Salt-Treated Group (250 mg/kg,p.o) | Potassium Salt-Treated Group (250 mg/kg,p.o.) |
|---|---|---|---|
| Amount of Gastric Juice Secreted (ml) | 4.9 ± 0.4 | 3.3 ± 0.4* | 3.5 ± 0.4* |
| Acidity of Gastric Juice (mEq/l) | 92.5 ± 3.7 | 58.4 ± 11.7* | 60.2 ± 11.8* |
| Activity of Pepsin (mg/ml) | 7.4 ± 0.5 | 5.0 ± 0.4** | 5.2 ± 0.4** |

Notes:
"p.o." stands for "per os (= by mouth)".
*The difference between the treated and control groups was significant at 5% level by T-test.
**The difference between the treated and control groups was significant at the 1% level by T-test.

(3) Acute Toxicity

Male and female mice of the dd Y strain, 4 weeks of age, as well as male and female rats of the rats of the Wistar strain, 7 weeks of age, were used in groups of ten. They were preliminarily raised for a week. Then, a compound to be tested (sodium salt) was dissolved in physiological saline solution and administered orally or subcutaneously. In the case of oral administration, the highest possible doses of 0.2 ml/10 g for mice and 2 ml/100 g for rats were used which both corresponded to 5,000 mg/kg. In the case of subcutaneous administration, the doses were reduced to ½. After the administration, the animals were observed for 7 days to detect the development of abnormalities. The animals that died during this period of observation were subjected to post-mortem examination. The results obtained are given in Table 3.

Table 3

| Animal Species | Acute Toxicity of a Compound of This Invention in Mice and Rats | |
|---|---|---|
| | $LD_{50}$ Values (mg/kg) of Sodium Salt | |
| | Subcutaneous | Oral |
| Mouse | >2,500 | >5,000 |
| Rat | >2,500 | >5,000 |

DESCRIPTION OF THE PREFERRED EMBODIMENTS

As is evident from the above-described experiments, the compounds of the present invention show excellent anti-ulcer effects and have utility in the field of pharmaceutical industry. In the treatment of adult patients with peptic ulcer, these compounds are preferably administered in a daily dose of from 500 to 3,000 mg, depending on the dosage form and the manner of division.

Like other gastrointestinal drugs, the compositions of this invention may be formed into oral preparations by any of conventional procedures. In order to exhibit their efficacy in the gastrointestinal tract, they may take a variety of dosage forms such as tablets, capsules, granules, dry syrups, solutions, etc., depending on the symptoms of the patient and other factors.

In the preparation of tablets which are a popular form for oral administration, inositol hexasulfate or an alkaline metal salt thereof is mixed with an excipient for oral use comprising one or more diluents selected from lactose, starch, crystalline cellulose, calcium phosphate, calcium carboxymethylcellulose, etc., in the proportion of 10 parts by weight of active ingredient to 1-10 parts by weight of excipient. If desired, a binder such as gelatin, polyvinyl pyrrolidone, hydroxypropylcellulose, etc. is added in the form of a solution. The resulting mixture is granulated by conventional procedure and, after the addition of a lubricant such as calcium stearate, talc, silicic anhydride, etc., formed into tablets by means of a tableting machine. The tablets may further be sugar-coated or film-coated by conventional procedure.

In the preparation of granules, inositol hexasulfate or (an alkaline metal) salt thereof is mixed with an excipient comprising one or more members selected from the above-enumerated diluents, sucrose mannitol, etc., in the proportion of 10 parts by weight of active ingredient to 1-10 parts by weight of excipient. Then, a binder as described above is added in the form of a solution. The resulting mixture is granulated and dried by conventional procedure.

Two typical formulas for the preparation of tablets and granules are given below.

| | |
|---|---|
| (1) Each tablet (280 mg) contains: | |
| Active ingredient | 250 mg |
| Corn starch | 25 mg |
| Hydroxypropylcellulose | 2 mg |
| Calcium stearate | 3 mg |
| (2) Each gram of granular preparation contains: | |
| Active ingredient | 900 mg |
| Corn starch | 50 mg |
| Crystalline cellulose | 40 mg |
| Hydroxypropylcellulose | 10 mg |

In view of the gastrointestinal indications for the use of the compositions of this invention, their oral preparations are very likely to be combined with other active ingredients. In practice, they can be stably combined, for example, with other gastrointestinal drugs including various antacids such as dried aluminum hydroxide gel, magnesium aluminate metasilicate, magnesium silicate, etc.

What is claimed is:

1. An anti-ulcer pharmaceutical composition comprising as an active ingredient a therapeutically effective amount of a compound selected from the group consisting of inositol hexasulfate, a sodium salt of inositol hexasulfate of the formula

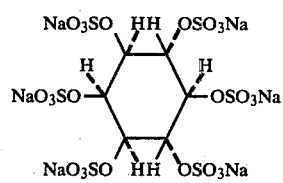

and a potassium salt of inositol hexasulfate of the formula

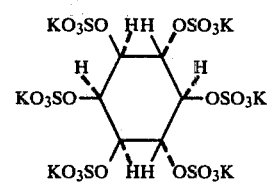

and a pharmaceutically acceptable carrier.

2. An anti-ulcer pharmaceutical composition comprising as an active ingredient 10 parts by weight of a compound selected from the group consisting of inositol hexasulfate, a sodium salt of inositol hexasulfate of the formula

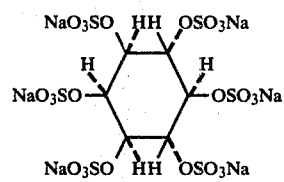

and a potassium salt of inositol hexasulfate of the formula

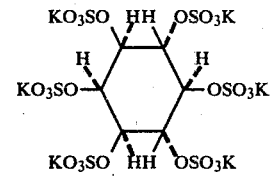

per 1-10 parts by weight of a pharmaceutically acceptable carrier.

* * * * *